United States Patent

Muchel

4,222,634

Sep. 16, 1980

[54] WIDE ANGLE OBJECTIVE FOR EXAMINATION OF THE EYE

[75] Inventor: Franz Muchel, Königsbronn, Fed. Rep. of Germany

[73] Assignee: Carl Zeiss Stiftung, Oberkochen, Fed. Rep. of Germany

[21] Appl. No.: 895,691

[22] Filed: Apr. 12, 1978

[30] Foreign Application Priority Data

Apr. 15, 1977 [DE] Fed. Rep. of Germany ....... 2716616

[51] Int. Cl.$^2$ ............................ G02B 3/04; G02B 9/00; A61B 3/14
[52] U.S. Cl. .................................... 350/189; 350/205; 350/231; 350/276 SL; 351/7
[58] Field of Search .............. 350/205, 276 SLA, 231, 350/189; 351/7

[56] References Cited

U.S. PATENT DOCUMENTS

3,914,032 10/1975 Takano et al. ........................... 351/7

*Primary Examiner*—Conrad J. Clark
*Attorney, Agent, or Firm*—Stonebraker, Shepard & Stephens

[57] ABSTRACT

A wide angle objective intended especially for visual and photographic examination of the fundus of the eye. Each of the separate lens elements which together make up the objective is so designed that one surface of the element provides the desired refractive power and the other surface of the same element is concentric with the locus of the pupil produced by the surface bearing the refractive power. Also, the objective is so designed that black points are arranged at the locus of the ghost reflections of the mirror conjugated with the pupil of the test subject which are produced in the objective, thereby suppressing disturbing reflections.

6 Claims, 1 Drawing Figure

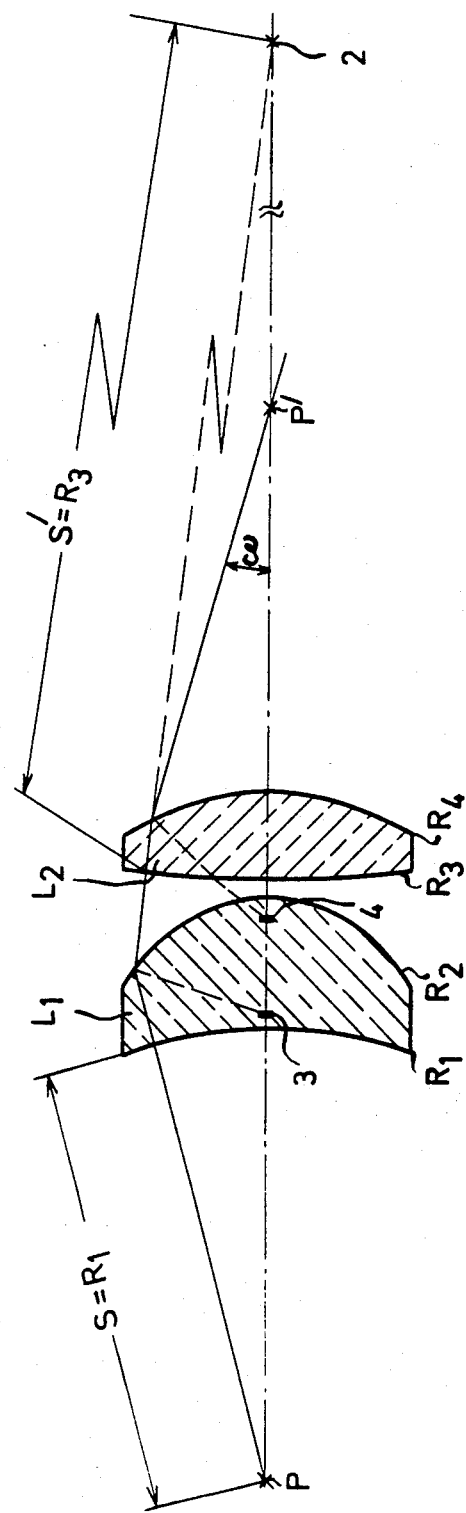

WIDE ANGLE OBJECTIVE FOR EXAMINATION OF THE EYE

BACKGROUND OF THE INVENTION

This invention relates to a wide angle objective for the visual and photographic examination of the fundus of the eye, in which disturbing light reflections are suppressed by light-arresting black points.

Objectives having a field of view of about 30 degrees are known for the examination of the retina of the eye. An object of the present invention is to provide an objective for the examination of the retina which permits a substantially larger angle of view than 30 degrees, preferably up to about 50 degrees.

This object is achieved, in accordance with the invention, by designing the individual lenses (lens elements) which make up the objective with such dimensions that one of the two surfaces of each lens provides the refractive power and the other surface of the same lens is concentric with the pupil locus produced by the surface which provides the refractive power. The surface providing the refractive power may be either spherical or aspherical.

Black points which suppress the reflections are advantageously provided in the objective at the locus of the ghost images produced.

The advantages obtained with this invention include especially the fact that large angles of view, for instance an angle of 50 degrees, are obtained with a design which is easy to carry out in practice.

BRIEF DESCRIPTION OF THE DRAWING

The single FIGURE is a diagrammatic or schematic representation of an objective in accordance with one illustrative embodiment of the invention.

DESCRIPTION OF THE PREFERRED EMBODIMENT

Referring now to the drawing, two lens elements which together form the objective for examination of the eye are illustrated schematically at $L_1$ and $L_2$. The surface of the lens $L_1$ which has the desired refractive power is designated $R_2$, and the surface of the lens $L_2$ which has the refractive power is designated $R_4$. The pupil of the patient's eye being examined is indicated at P', the location of the customary mirror and of the image of the pupil is indicated at P, and the virtual image of the patient's pupil P' is located at 2.

The respective opposite surfaces $R_1$ of the lens $L_1$ and $R_3$ of the lens $L_2$ are practically without refractive power with respect to the imaging of the pupil. The pupil locus of the patient's pupil P', which is produced by the surface $R_2$, lies in the mirror locus P to which the illumination is reflected. The surface $R_1$ is concentric with this locus P, the radius of this surface being equal to the axial spacing S from the locus P to the surface, as indicated in the diagram.

The pupil virtual image locus 2 is formed by the surface $R_4$. The surface $R_3$ is concentric with this pupil virtual image locus 2, as indicated by the notation on the diagram that $S' = R_3$.

The black points indicated schematically at 3 and 4 for supressing the ghost images of the mirror locus P which are produced by the surfaces $R_2$ and $R_4$ are located within the lens $L_1$, as illustrated.

With the embodiment of an objective in accordance with this invention as shown in the diagram, a field angle of 50 degrees is obtained.

What is claimed is:

1. A wide angle objective for visual and photographic examination of the fundus of the eye, comprising a plurality of lens elements collectively forming the objective, each element being formed with one surface which provides mainly the refractive power of the element and an opposite surface which is substantially concentric with a pupil locus produced by the first mentioned surface of the same element, said pupil locus being the locus of a real image or virtual image of the pupil of an eye being examined.

2. The invention defined in claim 1, wherein the surface of one element which provides refractive power is a spherical surface.

3. The invention defined in claim 1, wherein the surface of one element which provides refractive power is an aspherical surface.

4. The invention defined in claim 1, further comprising means forming black points, wherein the lens elements are so arranged and dimensioned that disturbing reflections are suppressed by light-arresting black points.

5. The invention defined in claim 4, wherein the lens elements are so arranged and dimensioned that said black points are located at the locus of ghost reflections of a mirror which is conjugated with the pupil of the eye being examined.

6. The invention defined in claim 4, wherein the lens elements are so arranged and dimensioned that said black points are located within one of said elements.

* * * * *